(12) United States Patent
Dawes et al.

(10) Patent No.: US 9,182,327 B2
(45) Date of Patent: Nov. 10, 2015

(54) SAMPLE PREPARATION BY SOLID PHASE EXTRACTION

(71) Applicant: TRAJAN SCIENTIFIC AUSTRALIA PTY LTD, Ringwood, Victoria (AU)

(72) Inventors: Ernest Frederick Dawes, Victoria (AU); Andrew Gooley, Victoria (AU)

(73) Assignee: TRAJAN SCIENTIFIC AUSTRALIA PTY LTD, Ringwood, Victoria (AU)

( * ) Notice: Subject to any disclaimer, the term of this patent is extended or adjusted under 35 U.S.C. 154(b) by 67 days.

(21) Appl. No.: 13/898,232

(22) Filed: May 20, 2013

(65) Prior Publication Data

US 2013/0330249 A1 Dec. 12, 2013

(30) Foreign Application Priority Data

May 18, 2012 (AU) ................................. 2012902066

(51) Int. Cl.
*B01D 21/00* (2006.01)
*G01N 1/40* (2006.01)
*G01N 1/14* (2006.01)

(52) U.S. Cl.
CPC ........ *G01N 1/405* (2013.01); *G01N 2001/1427* (2013.01)

(58) Field of Classification Search
CPC .................................................... G01N 1/405
USPC ...................... 422/527, 63–67, 536
See application file for complete search history.

(56) References Cited

U.S. PATENT DOCUMENTS

2004/0249341 A1 * 12/2004 Newbrough et al. ........... 604/87

* cited by examiner

*Primary Examiner* — Jyoti Nagpaul
(74) *Attorney, Agent, or Firm* — Fulwider Patton LLP

(57) ABSTRACT

A flow control assembly for use in preparation of samples for analysis by solid phase extraction includes a housing assembly having a first passage communicating with a needle bore and locating a solid phase sorbent, a second fluid port, and a valve for selective aspiration or delivery of fluid across a solid phase sorbent, or bypassing the solid phase sorbent. Independent flow paths are provided for a sample via the needle, and of the elution solvent via a separate port. The valve includes relatively slideable first and second members, the second member including an elongate shank that is relatively reciprocably slideable for effecting selective aspiration or delivery of fluid between first and second relative positions. A third fluid port may be provided communicating with the elongate second passage for selective fluid communication with a port in a shank when the shank is at the second relative position.

22 Claims, 2 Drawing Sheets

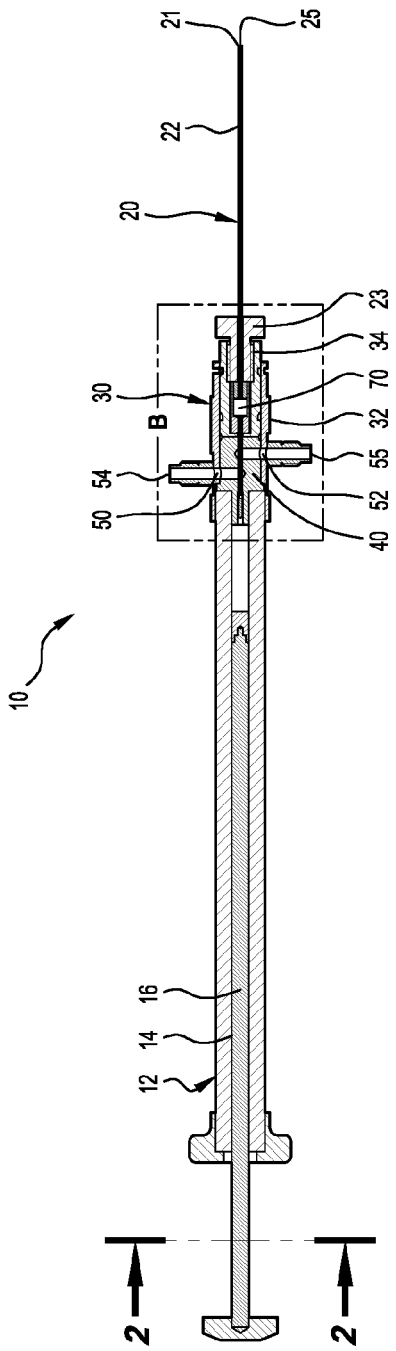
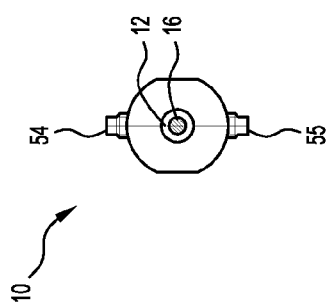
*Figure 1*
*Figure 2*

SAMPLE PREPARATION BY SOLID PHASE EXTRACTION

CROSS-REFERENCES TO RELATED APPLICATIONS

This application claims priority from Australian Application No. 2012902066, filed May 18, 2012 incorporated by reference in its entirety.

BACKGROUND

This invention relates generally to the preparation of samples for analysis and is concerned more particularly with the sample preparation technique known as solid phase extraction (SPE). The invention provides apparatus and techniques for improved sample preparation by solid phase extraction and is especially applicable where very small samples are desired.

Solid phase extraction (SPE) is a sample preparation technique where an analyte of interest is concentrated from a dilute matrix as well as being exchanged into a preferred matrix that is compatible with the analysis process. Typically the analyte is bound to a solid phase support or sorbent, washed and then eluted in a small concentrated volume. Micro Extraction by Packed Sorbent (MEPS™) is a form of micro SPE where the chromatography solid phase (2-3 mg of silica or polymer) is packed into a modified needle of an analytical syringe. In this case, the sample is aspirated onto the solid phase sorbent, commonly called the bed, using the aspirating stroke of the syringe. The solid volume is washed and then the analyte of interest is eluted using a suitable small volume of elution solvent. MEPS is fast, efficient and cost-effective when compared to traditional cartridge-based solid phase extraction. In effect, MEPS integrates the sample preparation and injection into a single device, streamlining workflows as extracts can be introduced directly into the analytical instrumentation.

It is an object of the invention to provide for further improvements in the functionality of MEPS as an advantageous method of solid phase extraction for microsamples.

SUMMARY OF THE INVENTION

It has been realised that MEPS has one drawback relative to some traditional techniques of solid phase extraction in that MEPS is bidirectional, ie all solutions are aspirated through the solid phase sorbent bed in one direction and dispensed through the bed again in the opposite direction. It has been further realised that there would be significant advantages if a user had control over the direction that the sample and buffers are delivered across the solid state sorbent bed in MEPS. In accordance with the invention, this is achieved by means of a flow control assembly that provides control over the direction of liquid flow (control directional flow) by facilitating selective aspiration or delivery of fluid across the solid phase sorbent or in a fashion that bypasses the solid phase sorbent.

The arrangement thereby allows respective independent flow paths for the sample—via the needle—and of the elution solvent—via a separate port. Elution solvent can be applied from the top of the absorbent bed, thus minimizing dilution and opportunities for sample carryover. In this way, a concentrated band of sample extract can be directly infused into the detector for maximum assay sensitivity.

The invention accordingly provides, in a first aspect, a flow control assembly for use in preparation of samples for analysis by solid phase extraction, comprising a housing assembly adapted to be fitted as a coupling between a syringe barrel having a barrel chamber therein and a syringe needle that has a needle bore extending therealong and defines a first fluid port at its tip. The housing assembly includes structure defining a first passage arranged to be in fluid communication with the needle bore at its inner end and to locate a solid phase sorbent that contacts fluid traversing the first passage and adsorbs predetermined species. There is a second fluid port in said housing assembly and a valve arrangement for selectively communicating the barrel chamber with the first passage and thereby with the needle bore or with the second fluid port for facilitating selective aspiration or delivery of fluid to or from the first fluid port across said solid phase sorbent or to or from the second fluid port bypassing the solid phase sorbent.

In a second aspect, the invention provides a syringe assembly for preparation of samples for analysis by solid phase extraction, comprising a syringe barrel having a barrel chamber therein, a syringe needle having a needle bore that extends therealong and defining a first fluid port at its tip and a second fluid port. The syringe assembly further includes structure defining a first passage arranged to be in fluid communication with the needle bore at its inner end and to locate a solid phase sorbent that contacts fluid traversing the first passage and adsorbs predetermined species, and a valve arrangement for selectively communicating the barrel chamber with the first passage and thereby with the needle bore or with the second fluid port for facilitating selective aspiration or delivery of fluid to or from the first fluid port across the solid phase sorbent or to or from the second fluid port bypassing the solid phase sorbent.

The valve arrangement may comprise relatively slideable first and second members (of the housing assembly in the first aspect) wherein the first member has an elongate second passage in communication at a first location with the barrel chamber and at a second location with the second port, and the second member has an elongate shank with a longitudinally extending cavity therein forming part of or in fluid communication with the first passage, which shank is relatively reciprocably slideable in the second passage for effecting the selective aspiration or delivery of fluid.

The shank may be relatively reciprocally slidable in the elongate second passage between a first relative position in which a port from said cavity is in fluid communication with the barrel chamber and the second fluid port is closed off by the shank, and a second relative position in which fluid communication between the barrel chamber and the second fluid port is open and between the barrel chamber and the cavity is prevented.

Conveniently, the just mentioned functionality is achieved by having the port from the cavity in the shank open laterally from the cavity at a position sufficiently displaced from an end of the shank in the second passage.

The aforesaid relative sliding movement is advantageously achieved by having said first member axially fixed within a cylindrical casing of the housing assembly and the second member slideably engageable within the casing. Preferably, the second member also carries the solid phase sorbent and the syringe needle.

In an advantageous embodiment, there is a third fluid port in communication with the elongate second passage for selective fluid communication with the port in the shank, advantageously when the shank is at the aforesaid second relative position.

BRIEF DESCRIPTION OF THE DRAWINGS

The invention will now be further described, by way of example only, with reference to the accompanying drawings, in which:

FIG. 1 is an axial cross-sectional view of a syringe assembly according to an embodiment of the invention, suitable for use in the preparation of samples for analysis by solid phase extraction according to the MEPS™ concept, wherein the flow control assembly is in an operating condition for practising conventional MEPS™ sample preparation;

FIG. 2 is a transverse cross-section on the line 2-2 in FIG. 1;

DETAILED DESCRIPTION OF THE PREFERRED EMBODIMENTS

Figure 3:
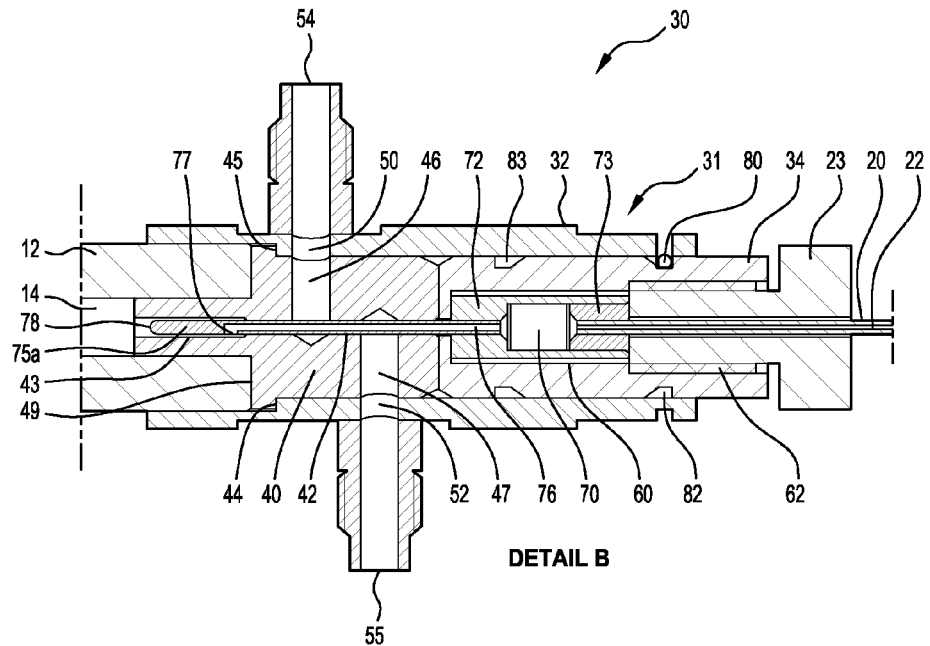
FIG. 3 is an enlargement of the portion B of FIG. 1.

The illustrated syringe assembly 10 is a modified form of syringe assembly for preparing samples by the aforedescribed MEPS™ technique of solid phase extraction. The syringe assembly 10 includes a syringe barrel 12 with a barrel chamber 14 in which plunger 16 is reciprocably slideable. The assembly further includes a syringe needle 20 having a longitudinally extending bore 22 that opens at its tip 21 to provide a first fluid port 25. The assembly depicted is manually operated but may of course alternatively be an auto-syringe system.

Serving as a coupling between the syringe barrel 12 and the syringe needle 20 is a flow control assembly or valve 30. A two-part housing 31 (FIG. 3) comprises generally tubular relatively slidable first and second members of the housing 31 in the form of outer and inner casings 32, 34. Outer casing 32 slideably receives inner casing 34 at one end and also includes and locates a generally cylindrical insert 40 at the other end. Outer casing 32 has a pair of offset diametrically opposite side fluid ports 50, 52 that extend into its hollow interior and are fitted with associated spigot couplings 54, 55 for receiving appropriate fluid conduits.

Insert 40 has a central through-bore 42 and a home position defined by complementary shoulders 44, 45 on the insert and casing 32 at which radial passages 46, 47 in the insert 40 register with ports 50, 52 to provide fluid communication with through-bore 42.

At its outer end insert 40 protrudes slightly beyond the adjacent end of casing 32 but is peripherally substantially rebated at 49 to accommodate the end of syringe barrel 12 in a firm fit. Within this reduced end portion of insert 40, through-bore 42 is counterbored to provide an enlarged end cavity 43, for a purpose that will become apparent.

Inner tubular housing 34 has respective smaller diameter and larger diameter coaxial inner and outer cavities 60, 62 that respectively house a solid phase sorbent cartridge 70 (also referred to herein as a MEPS™ cartridge) and mount syringe needle 20. Solid phase sorbent cartridge 70 is itself interchangeably housed in a counterbore of a cylindrical insert 72 and retained therein by a collar 73. A T-section adaptor 23 coaxially carries needle 20 and threadably engages cavity 62 to retain insert 72 and collar 73 so that the inner end of needle 20 extends through the collar and abuts the solid phase sorbent cartridge 70 to provide fluid flow communication between the solid phase and the first fluid port 25 at the needle tip 21. On the other, inner, side of solid phase sorbent cartridge 70 a fine cylindrical shank 75 is firmly secured in the bore of insert 72 and projects rearwardly therefrom. Shank 75 has a fine longitudinally extending central cavity 76 that extends from cartridge 70 to a lateral port or side hole 77 that opens laterally from cavity 76 at a position set back from the tip 78 of the shank to define a solid end portion 75a. Shank 75 is slideably and sealingly received by central through-bore 42 of insert 40. Side hole 77 may, for example, be 2-5 mm from the tip 78, say 3 mm or so.

Cavity 76 of shank 75 together with inner and outer cavities 60, 62 constitute a first passage that is in communication with the needle bore 22 and locates the solid phase sorbent cartridge 70. Through-hole 42 of insert 40, including enlarged end cavity 43, constitute a second passage in communication at a first location with barrel chamber 14 and at a second location with side port 50.

Figure 4:
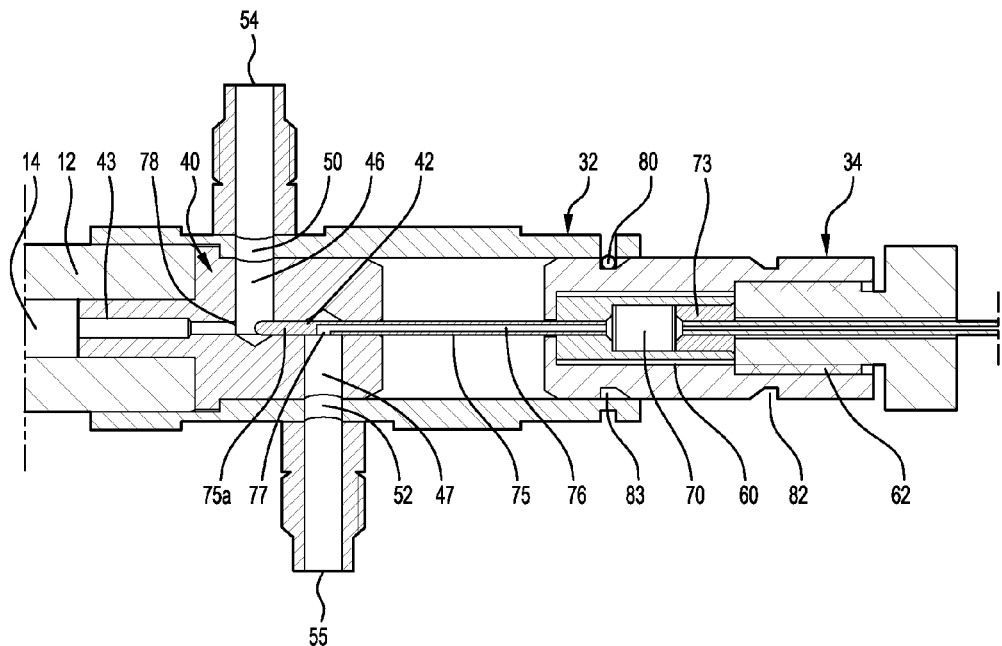
FIG. 4 is a view similar to FIG. 3 in which the flow control assembly has been adjusted to its alternative operating condition.

Inner tubular casing 34 is telescopically axially slideable (by hand as illustrated, or via an actuator) relative to tubular casing 32 between a first, inner, relative position depicted in FIG. 3, in which casing 34 abuts insert 40, and an outer relative position depicted in FIG. 4. These positions are indexed by engagement of a spring clip 80 or other suitable inwardly biased element with respective annular grooves 82, 83 in the outer surface of inner tubular casing 34.

In the first relative position depicted in FIGS. 1 and 3 ("Position 1"), the end portion 75a and side hole 77 of shank 75 extend through into enlarged end-cavity 43 of insert 40 so that there is fluid communication between the barrel chamber 14 and the aforesaid first passage, and thereby with first fluid port 25 at the tip of needle 21 via enlarged end-cavity 43, side hole 77, cavity 76, solid phase sorbent cartridge 70 and the bore 22 of needle 20. Fluid flow to and from side ports 50, 52 is prevented by the traversal of shank 75 across radial passages 46, 47.

In the outer relative position of the assembly, depicted in FIG. 4 ("Position 2"), the shank 75 is withdrawn to a position where side hole 77 opens into radial passage 47 and there is direct fluid communication between barrel chamber 14 and side port 50. It will be seen that the end portion 75a of shank 75 remains sufficiently advanced to prevent fluid communication between ports 50, 52.

It will be appreciated that in the first relative position of the assembly, conventional MEPS technique is practised. When the sample is aspirated, it moves into the barrel chamber 14 and passes through the solid phase sorbent. The needle can now be washed in this position or, if preferred, the control assembly is adjusted to the other relative position and the wash buffer can be aspirated through side port 50 into the syringe barrel, bypassing the solid phase. Once the wash solution is aspirated through side port 50, the flow control assembly is readjusted back to the inner relative position and the wash is dispensed through the solid phase sorbent and the needle.

To elute the target analyte from the solid phase, the flow control assembly is moved into the outer relative position and the elution solvent is aspirated into the syringe barrel through side port 50. While the device in this position, the operator has the option of using, for example, nitrogen or vacuum to dry the solid phase via the other side port 52. Alternatively, this other side port 52 may be simply closed off and the flushing option not adopted. Once the elution solvent is aspirated, the operator again returns the flow control assembly to the inner relative position and elutes the analyte from the solid phase sorbent.

In a simpler embodiment, radial passage 47 and side port 52 are not provided and side hole 77 is sealingly closed by the sealing sliding engagement of shank 75 in through-bore 42.

Table 1 sets out four alternative process sequences employing the two available positions (Positions 1 and 2 above) of the illustrated flow control assembly.

The advantages of this approach, made possible by the illustrated embodiment, are that an operator has an option of independent flow paths for the sample and the elution solvent, and that the concentration of the analyte can thereby be maximised by eluting from the solid phase sorbent in the smallest possible volume of elution solvent. This can be achieved by taking small fractions of the elution solvent such as 5 μL and then analysing each fraction to detect the presence of the analyte. Alternatively, a concentrated band of sample extract can be directly infused into a detector, such as a mass spectrometer, for maximum assay sensitivity.

The above technique overcomes the one drawback of MEPS in certain situations that the bound sample is necessarily diluted into the entire volume of the elution solvent. Conventional cartridge-based solid phase extraction is unidirectional (ie the sample is loaded on top of the sorbent bed as are the wash and elution solvents) whereas MEPS according to its current practice is bidirectional (all solutions are aspirated through the sorbent bed in one direction and dispensed through the bed in the opposite direction).

A further advantage of the side port providing an option to bypass the needle is the ability to employ much smaller particles in the solid phase sorbent. At present, the smallest particles that can be practically used are around 50 micron—any smaller and on an aspiration stroke it is very difficult to move the liquid through the bed. The smaller the particles the smaller the interstices. On aspiration with a needle one can only achieve a limited maximum pressure whereas much higher pressures can be obtained on a dispensing stroke. If one can operate through a side port, it should be possible to use particles as small as 5 or even 3 micron, which should substantially improve the efficiency of contact and binding.

In initial experiments in which the illustrated embodiment was attached to a digital syringe and the sample directly interfaced with a mass spectrometer electrospray source, a much improved intense peak of excellent Gaussian shape was achieved by the maximum concentration of the analyte. The complete analysis required a total analysis time ranging 5 to 12.5 min using this modified format of MEPS with controlled directional flow. The advantages included a sample elution without dilution, eliminating the need to optimize elution volumes. Direct carryover was reduced from 65% for conventional MEPS to only 1% for employing the illustrated arrangement MEPS, which removes the need for extensive wash cycles.

TABLE 1

Alternative Process Sequences

| Valve Position | | Valve Position | |
|---|---|---|---|
| | Standard Sequence | | Modified Sequence (elute from top) |
| 1 | Condition MEPS cartridge | 1 | Condition MEPS cartridge |
| 1 | Load sample (aspirate & dispense) | 1 | Load sample (aspirate & dispense) |
| 1 | Wash cartridge (aspirate & dispense) | 1 | Wash cartridge (aspirate & dispense) |
| 1 | Aspirate elution buffer | 2 | Aspirate elution buffer |
| 1 | Elute analyte | 1 | Elute analyte |
| | Modified Sequence with dry step | | Modified Sample Sequence (load from top when stationary phase particle size is <20 micron) |
| 1 | Condition MEPS cartridge | 1 | Condition MEPS cartridge |
| 1 | Load sample (aspirate & dispense) | 2 | Aspirate sample |
| | | 1 | Dispense sample |
| 2 | Aspirate air | 2 | Aspirate air |
| 1 | Dry cartridge | 1 | Dry cartridge |

TABLE 1-continued

Alternative Process Sequences

| Valve Position | | Valve Position | |
|---|---|---|---|
| 1 | Wash cartridge (aspirate & dispense) | 1-2 | Wash cartridge (aspirate [2] & dispense [1]) |
| 2 | Aspirate elution buffer | 2 | Aspirate elution buffer |
| 1 | Elute analyte | 1 | Elute analyte |

What is claimed is:

1. A flow control assembly for use in preparation of samples for analysis by solid phase extraction, comprising:
a housing assembly adapted to be fitted as a coupling between a syringe barrel having a barrel chamber therein and a syringe needle that has a needle bore extending therealong and defines a first fluid port at its tip, which housing assembly includes structure defining a first passage arranged to be in fluid communication with the needle bore at its inner end and to locate a solid phase sorbent that contacts fluid traversing said first passage and adsorbs predetermined species;
a second fluid port in said housing assembly; and
a valve arrangement for selectively communicating the barrel chamber with said first passage and thereby with the needle bore or with the second fluid port for facilitating selective aspiration or delivery of fluid to or from said first fluid port across said solid phase sorbent or to or from said second fluid port bypassing the solid phase sorbent.

2. A flow control assembly according to claim 1 wherein said valve arrangement comprises relatively slidable first and second members of said housing assembly wherein the first member has an elongate second passage in communication at a first location with the barrel chamber and at a second location with the second fluid port, and the second member has an elongate shank with a longitudinally extending cavity therein forming part of or in fluid communication with said first passage, which shank is relatively reciprocably slideable in said elongate second passage for effecting said selective aspiration or delivery of fluid.

3. A flow control assembly according to claim 2 wherein the shank is relatively reciprocably slideable in said elongate second passage, for effecting said selective aspiration or delivery of fluid, between a first relative position in which a port from said cavity is in fluid communication with the barrel chamber and the second fluid port is closed off by the shank, and a second relative position in which fluid communication between the barrel chamber and the second fluid port is open and between the barrel chamber and said cavity is prevented.

4. A flow control assembly according to claim 3 wherein said port from said cavity opens laterally from said cavity at a position sufficiently displaced from an end of the shank in said second passage.

5. A flow control assembly according to claim 3 further comprising a third fluid port in said housing assembly in communication with said elongate second passage for selective fluid communication with said port from the cavity in the shank.

6. A flow control assembly according to claim 5 wherein said third fluid port is in fluid communication with the port in said shank when the shank is at said second relative position.

7. A flow control assembly according to claim 5 wherein said port from said cavity opens laterally from said cavity at a position sufficiently displaced from an end of the shank in said second passage.

8. A flow control assembly according to claim 5 wherein the second member also carries the solid phase sorbent and the syringe needle when the flow control assembly is in situ coupling a syringe barrel to a syringe needle.

9. A flow control assembly according to claim 2 wherein the second member also carries the solid phase sorbent and the syringe needle when the flow control assembly is in situ coupling a syringe barrel to a syringe needle.

10. A flow control assembly according to claim 9 wherein the shank is relatively reciprocably slideable in said elongate second passage, for effecting said selective aspiration or delivery of fluid, between a first relative position in which a port from said cavity is in fluid communication with the barrel chamber and the second fluid port is closed off by the shank, and a second relative position in which fluid communication between the barrel chamber and the second fluid port is open and between the barrel chamber and said cavity is prevented.

11. A flow control assembly according to claim 10 wherein said port from said cavity opens laterally from said cavity at a position sufficiently displaced from an end of the shank in said second passage.

12. A syringe assembly for preparation of samples for analysis by solid phase extraction, comprising:
   a syringe barrel having a barrel chamber therein;
   a syringe needle having a needle bore that extends therealong and defining a first fluid port at its tip;
   a second fluid port;
   structure defining a first passage arranged to be in fluid communication with the needle bore at its inner end and to locate a solid phase sorbent that contacts fluid traversing said first passage and adsorbs predetermined species; and
   a valve arrangement for selectively communicating the barrel chamber with said first passage and thereby when the needle bore or with the second fluid port for facilitating selective aspiration or delivery of fluid to or from the first fluid port across the solid phase sorbent or to or from the second fluid port bypassing the solid phase sorbent.

13. A syringe assembly according to claim 12 wherein said valve arrangement comprises relatively slidable first and second members wherein the first member has an elongate second passage in communication at a first location with the barrel chamber and at a second location with the second fluid port, and the second member has an elongate shank with a longitudinally extending cavity therein forming part of or in fluid communication with said first passage, which shank is relatively reciprocably slideable in said elongate second passage for effecting said selective aspiration or delivery of fluid.

14. A syringe assembly according to claim 13 wherein the shank is relatively reciprocably slideable in said elongate second passage, for effecting said selective aspiration or delivery of fluid, between a first relative position in which a port from said cavity is in fluid communication with the barrel chamber and the second fluid port is closed off by the shank, and a second relative position in which fluid communication between the barrel chamber and the second fluid port is open and between the barrel chamber and said cavity is prevented.

15. A syringe assembly according to claim 14 wherein said port from said cavity opens laterally from said cavity at a position sufficiently displaced from an end of the shank in said second passage.

16. A syringe assembly according to claim 14 further comprising a third fluid port in communication with said elongate second passage for selective fluid communication with said port from the cavity in said shank.

17. A syringe assembly according to claim 16 wherein said third fluid port is in fluid communication with the port in said shank when the shank is at said second relative position.

18. A syringe assembly according to claim 16 wherein said port from said cavity opens laterally from said cavity at a position sufficiently displaced from an end of the shank in said second passage.

19. A syringe assembly according to claim 16 wherein the second member also carries the solid phase sorbent and the syringe needle.

20. A syringe assembly according to claim 13 wherein the second member also carries the solid phase sorbent and the syringe needle.

21. A syringe assembly according to claim 20 wherein the shank is relatively reciprocably slideable in said elongate second passage, for effecting said selective aspiration or delivery of fluid, between a first relative position in which a port from said cavity is in fluid communication with the barrel chamber and the second fluid port is closed off by the shank, and a second relative position in which fluid communication between the barrel chamber and the second fluid port is open and between the barrel chamber and said cavity is prevented.

22. A syringe assembly according to claim 21 wherein said port from said cavity opens laterally from said cavity at a position sufficiently displaced from an end of the shank in said passage.

* * * * *